US011191673B2

(12) United States Patent
Sargeant et al.

(10) Patent No.: US 11,191,673 B2
(45) Date of Patent: *Dec. 7, 2021

(54) CLOSURE TAPE DISPENSER

(71) Applicant: Covidien LP, Mansfield, MA (US)

(72) Inventors: Timothy Sargeant, Guilford, CT (US);
Arpan Desai, Hamden, CT (US);
Joshua Stopek, St. Louis Park, MN
(US); Atu Agawu, Princeton, NJ (US);
Saumya Banerjee, Hamden, CT (US);
Frank Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 352 days.

This patent is subject to a terminal disclaimer.

(21) Appl. No.: 15/437,466

(22) Filed: Feb. 21, 2017

(65) Prior Publication Data
US 2017/0156934 A1 Jun. 8, 2017

Related U.S. Application Data

(63) Continuation of application No. 13/778,813, filed on Feb. 27, 2013, now Pat. No. 9,572,580.
(Continued)

(51) Int. Cl.
A61F 13/02 (2006.01)
A61F 15/00 (2006.01)
(Continued)

(52) U.S. Cl.
CPC ...... *A61F 13/0266* (2013.01); *A61B 17/0057* (2013.01); *A61B 17/0218* (2013.01);
(Continued)

(58) Field of Classification Search
CPC ............. A61B 17/085; A61B 17/0057; A61B 17/3421; A61B 17/3417;
(Continued)

(56) References Cited

U.S. PATENT DOCUMENTS 4,359,049 A 11/1982 Redl et al.
4,874,368 A 10/1989 Miller et al.
(Continued)

FOREIGN PATENT DOCUMENTS

EP 2359782 A1 8/2011
EP 2361567 A1 8/2011
(Continued)

OTHER PUBLICATIONS

European Search Report EP13159340 dated Aug. 1, 2014.
(Continued)

*Primary Examiner* — Tan-Uyen T Ho
*Assistant Examiner* — Rachel S Highland
(74) *Attorney, Agent, or Firm* — Carter, DeLuca & Farrell LLP

(57) ABSTRACT

A surgical portal apparatus includes a sleeve having a proximal end and a distal end that extends along a longitudinal axis, and a surgical tape. The sleeve includes an inner wall defining an internal longitudinal passageway dimensioned for permitting passage of a surgical object therethrough and an outer wall configured for positioning against tissue. The inner and outer walls define at least a partial annular space therebetween, the annular space being in fluid communication with an opening in the outer wall. The surgical tape includes a body portion retained within the annular space of the sleeve and a leading tab extendable through the opening in the outer wall of the sleeve. The surgical tape has a first surface and a second surface, each of the first and second surfaces having at least one of tissue reactive functional groups and self-reactive functional groups.

21 Claims, 5 Drawing Sheets

Related U.S. Application Data

(60) Provisional application No. 61/611,706, filed on Mar. 16, 2012.

(51) Int. Cl.

| | | |
|---|---|---|
| *A61B 17/00* | (2006.01) | |
| *A61B 17/34* | (2006.01) | |
| *A61B 17/08* | (2006.01) | |
| *A61B 17/02* | (2006.01) | |
| *A61F 13/00* | (2006.01) | |

(52) U.S. Cl.
CPC ........ *A61B 17/085* (2013.01); *A61B 17/3417* (2013.01); *A61B 17/3421* (2013.01); *A61F 13/0206* (2013.01); *A61F 15/002* (2013.01); *A61B 2017/00004* (2013.01); *A61B 2017/0065* (2013.01); *A61B 2017/00606* (2013.01); *A61B 2017/00623* (2013.01); *A61B 2017/00637* (2013.01); *A61B 2017/0225* (2013.01); *A61F 2013/00357* (2013.01)

(58) Field of Classification Search
CPC ........... A61B 2017/00623; A61B 2017/00606; A61B 2017/00637; A61B 2017/0065; A61F 15/002
See application file for complete search history.

(56) References Cited

U.S. PATENT DOCUMENTS

| | | | |
|---|---|---|---|
| 4,978,336 A | 12/1990 | Capozzi et al. | |
| 4,979,942 A | 12/1990 | Wolf et al. | |
| 5,263,927 A | 11/1993 | Shlain | |
| 5,304,187 A * | 4/1994 | Green ................. | A61F 2/0063 604/13 |
| 5,368,563 A | 11/1994 | Lonneman et al. | |
| 6,333,051 B1 | 12/2001 | Kabanov et al. | |
| 6,416,506 B1 | 7/2002 | Tilton, Jr. et al. | |
| 6,527,749 B1 | 3/2003 | Roby et al. | |
| 6,632,929 B1 | 10/2003 | Wilchek et al. | |
| 6,638,508 B2 | 10/2003 | Schechter et al. | |
| 6,648,922 B2 | 11/2003 | Ung-Chhun et al. | |
| 7,699,191 B2 | 4/2010 | Sheets, Jr. et al. | |
| 7,858,079 B2 | 12/2010 | Hadba et al. | |
| 9,572,580 B2 | 2/2017 | Sargeant et al. | |
| 2002/0022266 A1 | 2/2002 | Wagner et al. | |
| 2002/0128234 A1 | 9/2002 | Hubbell et al. | |
| 2003/0022216 A1 | 1/2003 | Mao et al. | |
| 2003/0153001 A1 | 8/2003 | Soane et al. | |
| 2003/0181423 A1 | 9/2003 | Clapper et al. | |
| 2004/0023413 A1 | 2/2004 | Opalsky | |
| 2004/0092892 A1* | 5/2004 | Kagan ................. | A61F 2/04 604/264 |
| 2004/0193113 A1 | 9/2004 | Gillis et al. | |
| 2005/0119613 A1 | 6/2005 | Moenning et al. | |
| 2005/0153090 A1 | 7/2005 | Marchitto et al. | |
| 2005/0182443 A1 | 8/2005 | Jonn et al. | |
| 2005/0244453 A1 | 11/2005 | Stucke et al. | |
| 2005/0281802 A1 | 12/2005 | Gong et al. | |
| 2006/0025815 A1 | 2/2006 | McGurk et al. | |
| 2007/0073248 A1 | 3/2007 | Moenning | |
| 2007/0112361 A1 | 5/2007 | Schonholz et al. | |
| 2007/0286891 A1 | 12/2007 | Kettlewell et al. | |
| 2008/0161837 A1 | 7/2008 | Toso et al. | |
| 2008/0220029 A1 | 9/2008 | Ng et al. | |
| 2008/0221628 A1 | 9/2008 | Milbocker et al. | |
| 2008/0302487 A1 | 12/2008 | Goodman et al. | |
| 2009/0234376 A1 | 9/2009 | Soltz et al. | |
| 2010/0285088 A1 | 11/2010 | Sargeant et al. | |
| 2013/0110156 A1* | 5/2013 | Nakayama ............ | A61B 17/29 606/205 |
| 2013/0331868 A1* | 12/2013 | LePage, Jr. .......... | A61F 2/0063 606/151 |

FOREIGN PATENT DOCUMENTS

| | | |
|---|---|---|
| WO | 9423759 A1 | 10/1994 |
| WO | 0106829 A2 | 2/2001 |
| WO | 01/85077 A1 | 11/2001 |
| WO | 03/000234 A1 | 1/2003 |
| WO | 2006063249 A2 | 6/2006 |
| WO | 2007100882 A2 | 9/2007 |
| WO | 2011011347 A2 | 1/2011 |

OTHER PUBLICATIONS

European Search Report EP13159339 dated Aug. 1, 2014.
European Search Report EP 07751965.0 dated Aug. 27, 2012.
Huang et al., "Biotin-Derivatized Poly (L-lysine)-g-poly(ethylene glycol): A Novel Polymeric Interface for Bioaffinity Sensing" Laboratory for Surface Science and Technology, Department of Materials (2001) pp. 220-230.
Pardridge et al., Pharm. Res. vol. 15, No. 4, 576-582 (1998).
Jia, Z. et al., "Functional Disulfide-Stabilized Polymer-Protein Particles", Biomacromolecules, vol. 10, pp. 3253-3258 (2009).
Salmaso et al. Biochim. Biophys. Acta 1726, 57-66 (2005), available on line May 16, 2005.
Xie et al. Design of Attachment Type of Drug Delivery System by Complex Formation of Avidin With Biotinyl Drug Model and Biotinyl Saccharide, QActa Biomaterialia, 1, 2005, pp. 635-641.
International Search Report from corresponding EP Appln. No. 12192946.7 dated Feb. 1, 2013.

* cited by examiner

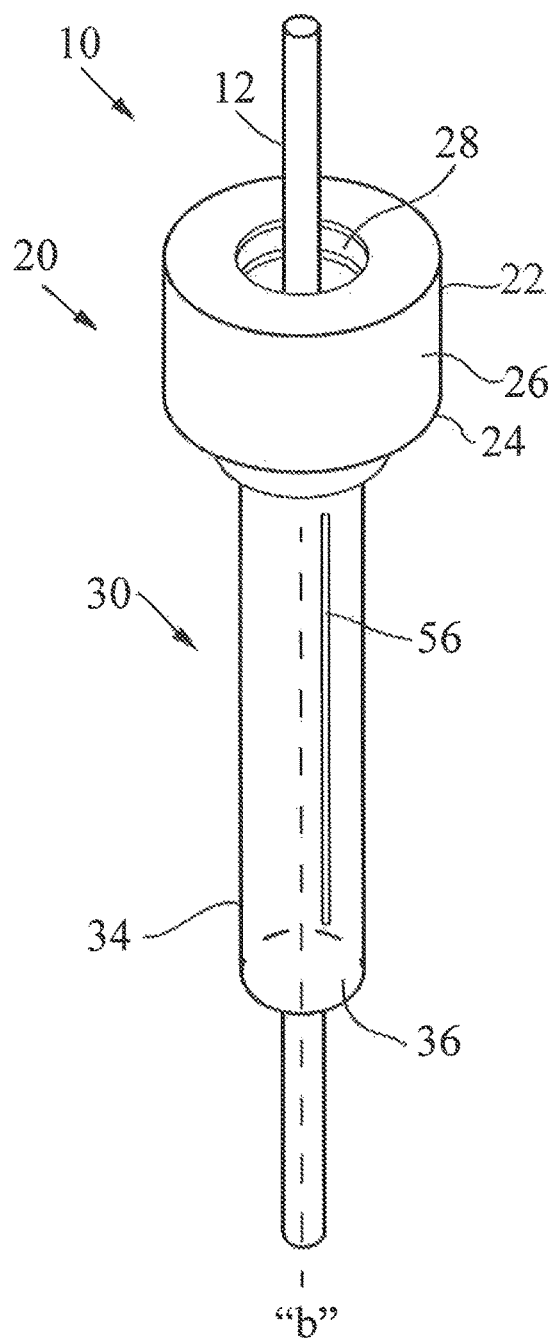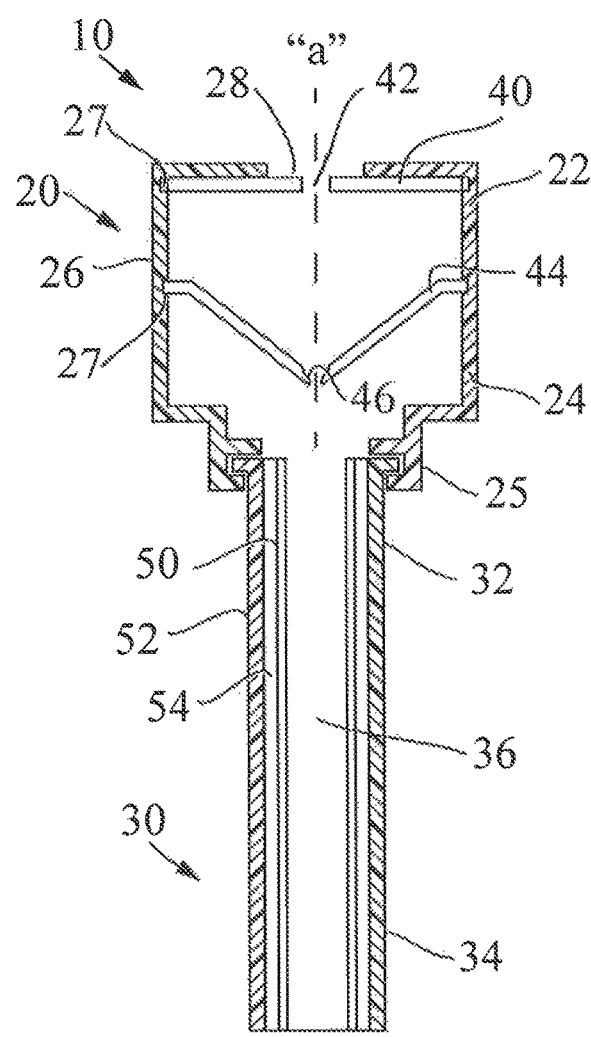
FIG. 1
FIG. 2

CLOSURE TAPE DISPENSER

CROSS-REFERENCE TO RELATED APPLICATIONS

This application is a continuation of U.S. patent application Ser. No. 13/778,813 filed Feb. 27, 2013, which claims the benefit of and priority to U.S. Provisional Patent Application No. 61/611,706, filed Mar. 16, 2012, and the disclosures of each of the above-identified applications are hereby incorporated by reference in their entirety.

BACKGROUND

1. Field of the Disclosure

The present disclosure relates to a surgical device and, more particularly, relates to a surgical portal apparatus for use during a minimally invasive surgical procedure including a surgical tape for sealing the wound through which the surgical portal apparatus was placed to access a surgical site.

2. Description of the Related Art

Many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

Generally, in minimally invasive surgical procedures, surgical portal apparatus, such as trocars and cannulas, permit the introduction of a variety of surgical instruments into a body cavity or incision. A surgical portal apparatus is introduced through a cavity or incision to provide access to an underlying surgical site in the body. The incision is typically made using an obturator having a blunt or sharp radius within the passageway of the surgical portal apparatus. For example, a trocar has a cannula, a tube of rigid, thin wall construction, through which an obturator may be distally passed. The obturator is utilized to penetrate a body wall, such as an abdominal wall, or to introduce the surgical portal apparatus through the body wall, and is then removed from the surgical portal apparatus to permit introduction of surgical instrumentation utilized to perform the procedure therethrough.

Post-surgery, wound closure devices, such as sutures, are used to close the various layers of tissue (e.g., dermis, facias, muscle, peritoneum, etc.) of the formed wound. Suturing a patient after removal of a surgical portal apparatus may be cumbersome, while accumulating additional costs to the patient such as increased time spent in the operating room. For example, manual suturing may take approximately 2-4 minutes per surgical portal apparatus, with 4-8 surgical portal apparatus typically being utilized per procedure.

It would be desirable to provide a surgical portal apparatus with an integrated wound closure material that can quickly and easily effect closure of a wound without the need for a separate applicator.

SUMMARY

A surgical portal apparatus in accordance with the present disclosure includes a sleeve having a proximal end and a distal end that extends along a longitudinal axis and a surgical tape. The sleeve includes an inner wall defining an internal longitudinal passageway dimensioned for permitting passage of a surgical object therethrough and an outer wall configured for positioning against tissue. The inner and outer walls define at least a partial annular space therebetween, the annular space being in fluid communication with an opening in the outer wall. The surgical tape includes a body portion retained within the annular space of the sleeve and a leading tab extendable through the opening in the outer wall of the sleeve. The surgical tape has a first surface and a second surface, each of the first and second surfaces having at least one of tissue reactive functional groups and self-reactive functional groups.

Methods of using the surgical portal apparatus are also described. In accordance with the present disclosure, a surgical portal, as described above, may be introduced into a body cavity through a wound in tissue. The leading tab of the surgical tape, which is configured to allow for placement of the surgical portal apparatus within the wound prior to substantial fixation with the tissue of the wound, is positioned against tissue. Surgical tasks are performed through the internal longitudinal passageway of the sleeve. The sleeve is then manipulated to release the body portion of the surgical tape within the tissue of the wound. The surgical portal apparatus is then removed and the wound closed.

BRIEF DESCRIPTION OF THE DRAWINGS

Embodiments of the present disclosure will be better appreciated by reference to the drawings wherein:

FIG. 1 is a perspective view of a surgical portal apparatus in the form of a seal housing and a portal sleeve in accordance with an embodiment of the present disclosure;

FIG. 2 is a cross-sectional view of the surgical portal apparatus of FIG. 1;

DETAILED DESCRIPTION

Figure 3:
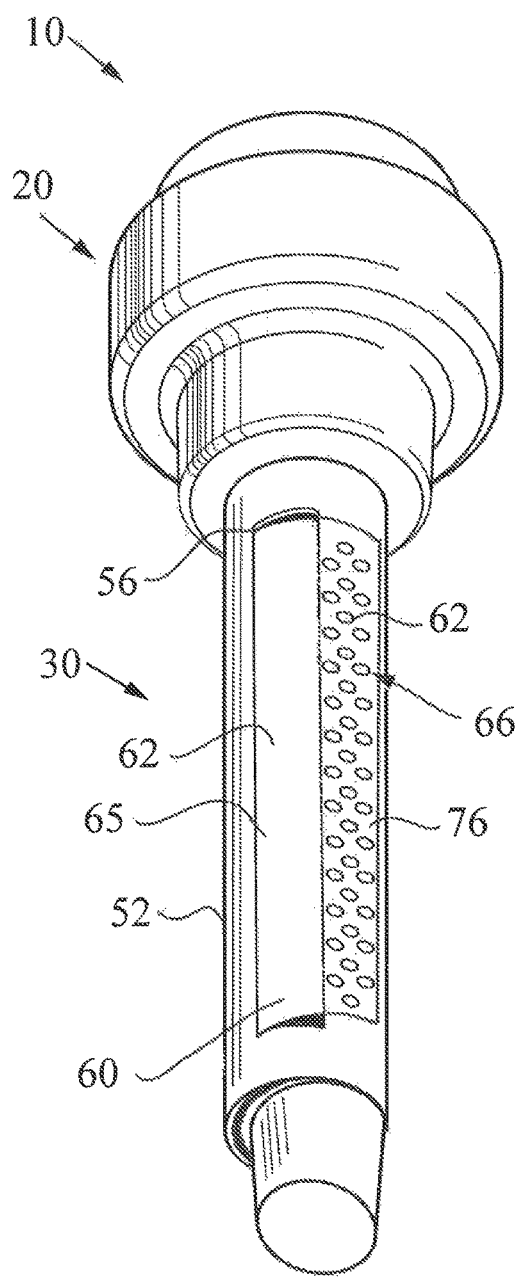
FIG. 3 is a perspective view of the surgical portal apparatus of FIGS. 1 and 2 including a surgical tape in accordance with an embodiment of the present disclosure.

Various exemplary embodiments of the present disclosure will be discussed hereinbelow in terms of a surgical portal apparatus for use during a surgical procedure. It should be understood that the principles of the present disclosure are equally applicable to a variety of surgical portal apparatus that may be inserted into an incision in a variety of surgical applications. For example, the surgical portal apparatus of the present disclosure may include, for example, trocars, cannulas, access ports such as SILS™ ports, introducers, and other surgical access devices within the purview of those skilled in the art.

The surgical portal apparatus of the present disclosure incorporates a seal housing in combination with a sleeve that is configured and adapted for introduction through tissue into a body cavity of a patient. The sleeve includes an inner wall and an outer wall defining an annular space therebetween that is dimensioned to retain a surgical tape. The surgical tape is released from the sleeve upon removal of the surgical portal apparatus from the tissue to close a wound.

Embodiments of the presently disclosed surgical portal apparatus will now be described in detail with reference to the drawing figures wherein like reference numerals identify similar or identical elements. In the following discussion, the term "proximal" should be understood as referring to the portion of a structure that is closer to a clinician during proper use, and the term "distal" should be understood as referring to the portion of a structure that is further from the clinician during proper use. As used herein, the term "patient" should be understood as referring to a human subject or other animal, and the term "clinician" should be understood as referring to a doctor, nurse or other care provider and may include support personnel.

Referring now to the drawings, FIGS. 1 and 2 illustrate an embodiment of a surgical portal apparatus 10 of the present disclosure. Portal apparatus 10 includes a seal housing 20 mounted to a sleeve 30.

Seal housing 20 includes a proximal end portion 22, a distal end portion 24, and a sidewall 26 connecting the proximal end portion 22 and the distal end portion 24. Proximal end portion 22 includes an aperture 28 aligned with a central housing axis "a" that is adapted for receiving surgical objects and instruments 12 of varying diameters therethrough. Examples of surgical objects and instruments which may be introduced through the surgical portal apparatus include clip appliers, graspers, dissectors, retractors, staplers, laser probes, photographic devices, endoscopes, laparoscopes, arthroscopes, tubes, electrosurgical cutting, coagulating, and ablation devices, and other tools within the purview of those skilled in the art.

The seal housing 20 may incorporate a seal 40 which, either alone or in combination with a valve 44, provides a substantial seal between a body cavity of a patient and the outside atmosphere before, during, and after insertion of a surgical instrument 12 through the surgical portal apparatus 10. A fluid tight interface is maintained via the seal 40 about the inserted surgical instrument 12. This substantially prevents gas and/or liquid leakage from the established surgical site so as to preserve the atmospheric integrity of a surgical procedure. Sidewall 26 may define one or more internal peripheral channels or recesses 27 for receiving a portion or component of the seal 40 and/or valve 44. Internal peripheral channel or recess 27 may be defined along any portion of the sidewall 26.

Seal 40 may be generally disc shaped and sized to fit within the seal housing 20. Seal 40 including an opening or slit 42 that is configured to form a fluid-tight fit about the surgical instrument 12. As illustrated in the current embodiment, the seal 40 is flat or planar. It is envisioned that the seal 40 may be any shape, such as having a tapered or funneled profile, for sealing and maintaining the integrity of the established surgical site. Seal 40 may be a gel seal, fabric seal, elastomeric seal, or combinations thereof.

Valve 44 may be placed distal, or internal to, the seal 40. Valve 44 may be a zero-closure valve such as a duck-bill valve having a slit 46 which is adapted to close in the absence of a surgical instrument 12 and/or in response to insufflation gases of the pressurized cavity. Further, valve 44 prevents fluids or debris from entering the seal housing 20 when the valve 44 is closed. Fluid pressure on the valve 44 will close the slit 46 thereby sealing the seal housing 20 from fluids. When a surgical object or instrument 12 is inserted through the valve 44, however, a seal is not always formed around the surgical instrument 12 thereby allowing some fluid to enter the seal housing 20 wherein the seal 40 prevent the fluid from exiting the seal housing 20. In the alternative, valve 44 may be a gel seal, balloon valve, or a flapper valve.

Distal end portion 24 of portal housing 20 including a joining member 25 for joining the seal housing 20 to the sleeve 30. Distal end portion 24 may be selectively releasably connectable to the sleeve 30 to cooperatively couple the seal housing 20 to the sleeve 30. Various means for releasably securing or connecting the seal housing 20 to the sleeve 30 are envisioned including a bayonet coupling, snap-fit, frictional fit, tongue and groove arrangement, threaded arrangement, cam-lock mechanisms, or the like. As illustrated in the current embodiment, seal housing 20 is secured to the sleeve 30 via snap fit. Seal housing 20 may be mounted to the sleeve 30 before, during, or after, application of the sleeve 30 within the operative site. Alternatively, seal housing 20 may be permanently secured to the sleeve 30 by conventions means, such as, for example, ultrasonic welding, use of adhesives, or by monolithically forming the seal housing 20 with the sleeve 30.

Sleeve 30 may be any portal member suitable for the intended purpose of accessing a body cavity and defines a central longitudinal axis "b" extending along the length of the sleeve 30 from a proximal end 32 to a distal end 34. As illustrated, the central longitudinal axis "b" of the sleeve 30 may be coincident with the central housing axis "a" of the seal housing 20 when the seal housing 20 is mounted to the sleeve 30. Sleeve 30 further defines an internal longitudinal passageway 36 dimensioned to permit introduction and passage of a surgical instruments 12 therethrough. Sleeve 30 may be transparent, translucent, or opaque and may be formed of any suitable medical grade material, such as metal materials, like stainless steel, titanium, and aluminum; polymeric materials, like acrylonitrile-butadiene-styrene, polycarbonate, and polystyrene; and other rigid materials and combinations thereof as envisioned by one skilled in the art. Sleeve 30 may or may not include means for facilitating retention of the sleeve 30 within tissue. Such means include a plurality of locking elements, ribs, or other locking arrangements within the purview of those skilled in the art.

With reference now to FIG. 3, in conjunction with FIGS. 1 and 2, sleeve 30 includes an inner wall 50 and an outer wall 52 defining a substantially cylindrical annular space 54 therebetween. The annular space 54 is dimensioned to receive a surgical tape 60, or other wound closure material. In embodiments, the outer wall 52 of the sleeve 30 includes, or is covered by, a non-adherent absorbent material, such as gauze, to remove excess fluid from tissue in which the sleeve 30 is placed thereby wiping and/or drying the surrounding tissue for application of the surgical tape 60 thereto.

Surgical tape 60 includes a body portion 65 which may be wrapped around the inner wall 50 of the sleeve 30 to retain the surgical tape 60 therein. An opening 56 is configured and dimensioned to allow passage of the surgical tape 60 from within the annular space 54 of the sleeve 30. In embodiments, the opening 56 is a longitudinal slot in the outer wall 52 of the sleeve 30 extending along a portion of the length of the sleeve 30, in some embodiments, along substantially the entire length of the sleeve 30. As illustrated, surgical tape 60 includes a leading tab 66 extending from the body portion 65 retained within the annular space 54 of the sleeve 30 through the opening 56.

Figure 5A:
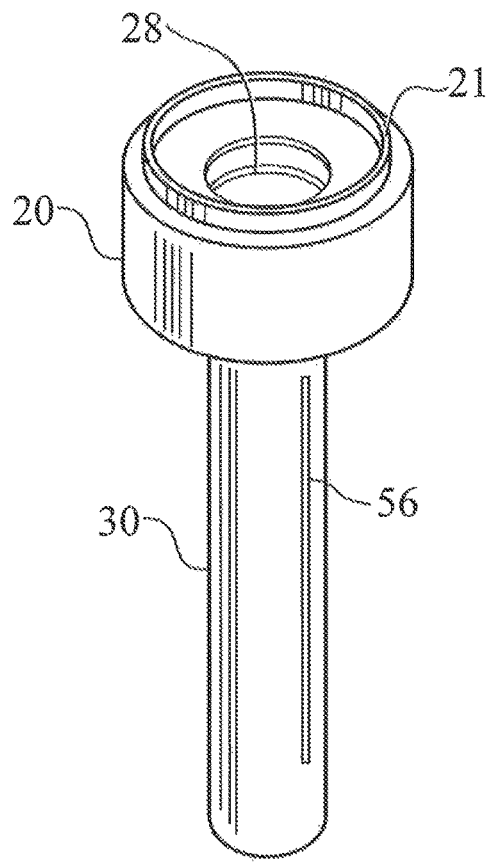
FIGS. 5A and 5B are a perspective view and a side cross-sectional view, respectively, of a surgical portal apparatus in accordance with another embodiment of the present disclosure.
Figure 5B:
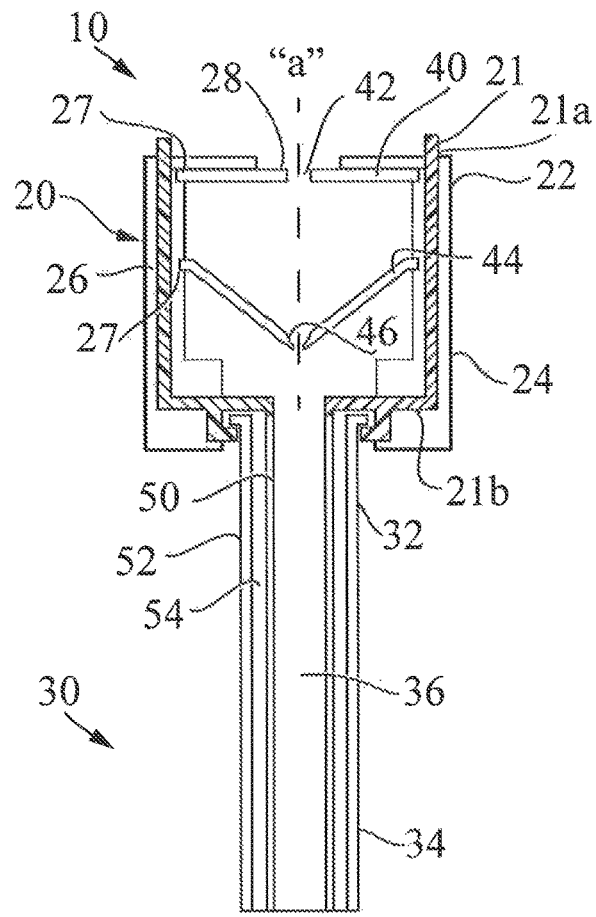
Figure 5C:
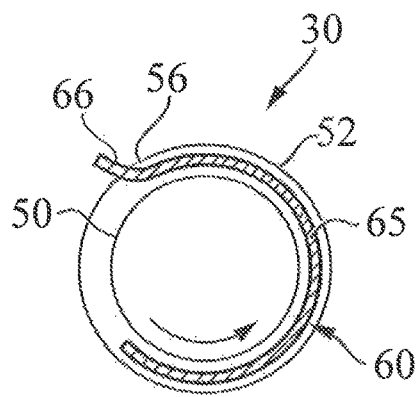
FIG. 5C is an axial cross-sectional view of the surgical portal apparatus of FIGS. 5A and 5B.

Alternatively, the leading tab 66 may be retained within the annular space 54 of the sleeve 30 and rotated out of the opening 56 in the outer wall 52 via a rotatable knob 21. As illustrated in FIGS. 5A and 5B, an upper portion 21a of the knob 21 extends through the seal housing 20 and a lower portion 21b is affixed to the inner wall 50 of the sleeve 30. Accordingly, manual rotation of the upper portion 21a of the knob 21 will rotate the inner wall 50 of the sleeve 30. As illustrated in FIG. 5C, for example, the leading tab 66 of the surgical tape 60 may be aligned with the opening 56 in the outer wall 52 of the sleeve 30 such that upon rotation of the knob 21 in the direction shown by the arrow, the surgical tape 60 is rotated out of the sleeve 30. In embodiments, at least a part of the body portion 65 of the surgical tape 60 may be temporarily affixed to the inner wall 50 to aid in the rotation of the surgical tape 60 with the inner wall 50.

Figure 5D:
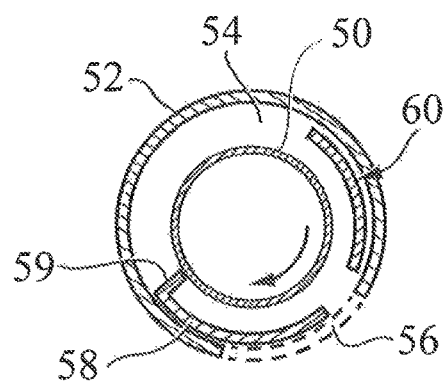
FIG. 5D is an axial cross-sectional view of the surgical portal apparatus of FIGS. 5A and 5B in accordance with an embodiment of the present disclosure.

In other embodiments, the opening 56 in the outer wall 52 may be covered by a retractable window or door 58. FIG. 5D illustrates a door 58 that is connected to the inner wall 50 of the sleeve 30. Rotation of the knob 21 (FIGS. 5A and 5B) moves the door 58 between a closed position in which the door 58 covers and seals the opening 56 in the outer wall 52 thereby protecting the surgical tape 60 within the annular space 54 of the sleeve 30, and an open position which allows for passage of the surgical tape 60 through the opening 56 in the outer wall 52. The door 58 may include a hinge 59 so that the door 58 may be positioned within the opening 56 in the outer wall 52 to form a continuous outer surface with the outer wall 52. The rotation of the knob 21 (FIGS. 5A and 5B) in the direction of the arrow shown in FIG. 5D, retracts the door 58 into the annular space 54 of the sleeve 30, unblocking the opening 56 in the outer wall 52. Other mechanical mechanisms within the purview of those skilled are also envisioned for actuating the door 58 in relation to the opening 56 in the outer wall 52.

Leading tab 66 may be an integral part of the body portion 65 of surgical tape 60 or may be independent thereof and attached thereto. It should be understood that the length of the opening 56 and the surgical tape 60 may vary depending upon the depth of incision and length of the sleeve 30 being utilized in a given surgical procedure. The surgical tape 60 may also be sized and dimensioned to extend across the width of the incision to effect closure of the tissue.

While a surgical tape is illustrated and described in the current embodiment, it should be understood that the surgical tape may be any medical device that may be used for wound closure device such as, for example, meshes, scaffolds, soft tissue repair devices, grafts, slings, gauzes, buttresses, pledgets, wound dressings, drug delivery devices, tissue wraps, as well as other substrates, implants, composite materials, or combinations thereof.

Surgical tape 60 is fabricated from any biocompatible material. Surgical tape 60 may be a biodegradable and/or non-biodegradable material which may be natural or synthetic. The term "biodegradable" as used herein is defined to include both bioabsorbable and bioresorbable materials. By biodegradable, it is meant that the material decomposes, or loses structural integrity under body conditions (e.g., enzymatic degradation or hydrolysis), or is broken down (physically or chemically) under physiologic conditions in the body, such that the degradation products are excretable or absorbable by the body. Absorbable materials are absorbed by biological tissues and disappear in vivo at the end of a given period, which can vary, for example, from hours to several months, depending on the chemical nature of the material. It should be understood that such materials include natural, synthetic, bioabsorbable, and/or certain non-absorbable materials, as well as combinations thereof. Surgical tapes 60 utilizing biodegradable materials enable quick and complete wound healing to occur without permanently leaving a foreign material within tissue, while surgical tapes 60 fabricated from non-biodegradable materials provide continuous reinforcement and support to tissue.

Non-limiting examples of natural biodegradable polymers from which the surgical tape may be made include: proteins such as collagen, gelatin, albumin, serum, and casein; poly (amino acids); polysaccharides such as cellulose (including carboxymethyl cellulose), dextran, chitin, chitosan, alginate and hyaluronic acid; glycosaminoglycans; gut; as well as chemical derivatives thereof (substitutions and/or additions of chemical groups, for example, alkyl, alkylene, hydroxylations, oxidations, and other modifications routinely made by those skilled in the art), copolymers, and combinations thereof. Collagen as used herein includes natural collagen such as animal derived collagen, or synthetic collagen such as recombinant collagen. Additionally, natural materials include chemical modifications of the above-listed materials such as recombinant, aminated, sulfonated, and carboxylated polymer analogs.

Non-limiting examples of synthetic biodegradable polymers which may be utilized to form the surgical tape include polyhydroxy acids prepared from lactone monomers (such as glycolide, lactide, caprolactone, ϵ-caprolactone, valerolactone, and δ-valerolactone), carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include, for example: polylactides; poly(lactic acid); polyglycolides; poly(glycolic acid); poly(trimethylene carbonate); poly(dioxanone); poly(hydroxybutyric acid); poly (hydroxyvaleric acid); poly(lactide-co-(ϵ-caprolactone-)); poly(glycolide-co-(ϵ-caprolactone)); polycarbonates; poly (pseudo amino acids); poly(amino acids); poly(hydroxyalkanoate)s such as polyhydroxybutyrate, polyhydroxyvalerate, poly(3-hydroxybutyrate-co-3-hydroxyvalerate), polyhydroxyoctanoate, and polyhydroxyhexanoate; polyalkylene oxalates; polyoxaesters; polyanhydrides; polyester anyhydrides; polyortho esters; and copolymers, block copolymers, homopolymers, blends, and combinations thereof.

Non-limiting examples of suitable nondegradable materials from which the surgical tape may be made include:

polyolefins such as polyethylene (including ultra high molecular weight polyethylene) and polypropylene including atactic, isotactic, syndiotactic, and blends thereof; polyethylene glycols; polyethylene oxides; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; etheylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof.

Surgical tape 60 may be porous, non-porous, or a combination thereof. In embodiments, the surgical tape 60 may be a film, foam, mesh, fibrous sheet, patch, or composite thereof including porous and/or non-porous layers of films, foams, and/or meshes. The term "porous" as used herein may define openings and spacings which are present as a surface characteristic or a bulk material property, partially or completely penetrating the surgical tape. Suitable materials for forming a porous substrate include, but are not limited to fibrous structures (e.g., knitted structures, woven structures, non-woven structures, etc.), foams (e.g., open or closed cell foams), and perforated films. Use of a porous substrate may allow for quicker healing through the openings formed therein.

In embodiments, the pores may be in sufficient number and size so as to interconnect across the entire thickness of the surgical tape. Woven fabrics, kitted fabrics, and open cell foam are illustrative examples of structures in which the pores can be in sufficient number and size so as to interconnect across the entire thickness of the substrate. In embodiments, the pores may not interconnect across the entire thickness of the substrate, but rather may be present at a portion thereof. Thus, in some embodiments, pores may be located on a portion of the surgical tape, with other portions of the surgical tape having a non-porous texture. Closed cell foam or fused non-woven materials are illustrative examples of structures in which the pores may not interconnect across the entire thickness of the substrate. Those skilled in the art reading the present disclosure will envision a variety of pore distribution patterns and configurations for the surgical tape.

Figure 4A:
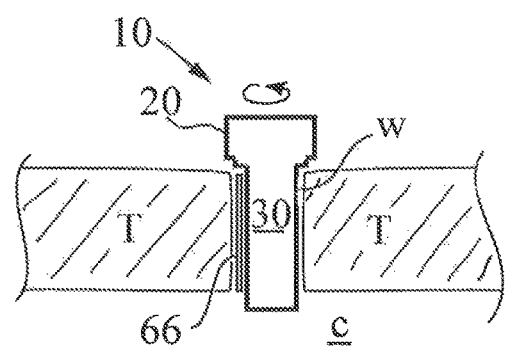
FIGS. 4A and 4B are cross-sectional schematic illustrations of the surgical portal apparatus of FIGS. 1-3 being positioned within tissue and removed from tissue, respectively, in accordance with an embodiment of the present disclosure.
Figure 4B:
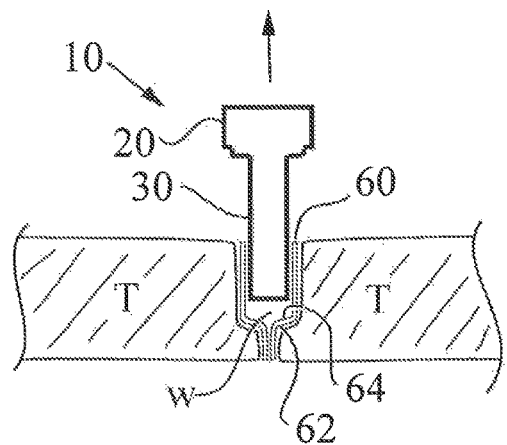

Surgical tape 60 includes a first surface 62 and a second surface 64 (FIG. 4B). The first and second surfaces 62, 64 of surgical tape 60 may include tissue reactive functional groups for fixation of the surgical tape 60 to tissue by crosslinking with reactive groups present in tissue "T" such as primary amine groups, secondary amine groups, hydroxyl groups, carboxylic groups, sulfonic groups, combinations thereof, and the like. Such groups include compounds possessing chemistries having some affinity for tissue.

For amine binding reactions, for example, isothiocyanates, isocyanates, acyl azides, N-hydroxysuccinimide (NETS) and sulfo-NHS esters, sulfonyl chlorides, aldehydes and glyoxals, epoxides and oxiranes, carbonates, arylating agents, imidoesters, carbodiimides, and anhydrides may be utilized. For carboxyl binding reactions, for example, diazoalkanes and diazoacetyl compounds may be utilized, as well as carbonyldiimidazoles, carbodiimides, and NETS, which convert carboxylic acid into a reactive intermediate which is susceptible to reaction with amines or alcohols. For hydroxyl binding reactions, for example, epoxides and oxiranes, carbonyldiimidazoles, disuccinimidyl carbonate and hydroxysuccinimidyl chloroformate, alkyl halogens, isocyanates, and methacryloyl or acryloyl chloride may be utilized, as well as oxidation with periodate or enzymatic oxidation. It is contemplated by the present disclosure that the functional groups may be the same or different at each occurrence. Thus, the surgical tape may have two or more different functional groups for binding to tissue.

In embodiments, the first and/or second surfaces 62, 64 may include self-reactive functional groups having a complementary functionality for securing the surgical tape 60 to itself. By "complementary" it is meant that the reactive groups are able to specifically interact together to bond the first and/or second surface 62, 64 together. The term "bonding" as used herein refers to all types of chemical and physical crosslinking including covalent, ionic, and hydrophobic bonding. Chemical (covalent) crosslinking may be accomplished by any of a number of mechanisms, including free radical polymerization, condensation polymerization, anionic or cationic polymerization, step growth polymerization, electrophile-nucleophile reactions, combinations thereof, and the like. In addition, physical (non-covalent) crosslinks may result from complexation, hydrogen bonding, desolvation, Van der Waals interactions, ionic bonding, combinations thereof, and the like.

In embodiments, the reactive groups are electrophilic or nucleophilic groups capable of reacting with tissue and/or each other to form a bond. Electrophilic functional groups include, for example, N-hydroxysuccinimides ("NETS"), sulfosuccinimides, carbonyldiimidazole, sulfonyl chloride, aryl halides, sulfosuccinimidyl esters, N-hydroxysuccinimidyl esters, succinimidyl esters such as succinimidyl succinates and/or succinimidyl propionates, isocyanates, thiocyanates, carbodiimides, benzotriazole carbonates, epoxides, aldehydes, maleimides, imidoesters, combinations thereof, and the like. In embodiments, the electrophilic reactive group is a succinimidyl ester.

Suitable nucleophilic groups include, but are not limited to, $-NH_2$, $-SH$, $-OH$, $-PH_2$, $-CO-NH-NH_2$ and combinations thereof. In embodiments, the nucleophilic reactive group is an amine.

In other embodiments, bonding may be accomplished with biological cross-linking systems, including for example, antibody/antigen; biotin/avidin; complementary peptide binding sequences; nucleotide base pairing and cross-linking; lock and key protein binding chemistry; self-assembling peptides; combinations thereof, and the like. In embodiments utilizing biotin and avidin reactive chemistries, biotin may be functionalized to include reactive groups such as amine, sulfhydryl, carbonyl, and carboxy, based upon the substrate to which it is to be bound. Avidin, streptavidin, and their derivatives, may be utilized for bonding with a substrate containing biotin or with endogenous biotin within tissue.

The material forming the surgical tape 60 may be functionalized to provide reactive groups for binding or attaching to tissue or to surfaces of the surgical tape itself. For example, amines may be provided on proteins, aminoglycans (such as chitosan, chondrotins, hyaluronic acid, and heparin), and polypeptides (like polylysine); carboxyl groups may be provided on proteins, polypeptides (like poly(glutamic acid)), polysaccharides (such as carboxylated dextran and carboxymethyl cellulose), and synthetic polymers (like carboxylated PEG and PEG-diadipate); hydroxyl groups may be provided on polysaccharides (like dextran), di-PEG adipate, and aliphatic polyesters (such as poly(lactic acid), poly(glycolic acid), poly(caprolactone), poly(trimethylene carbonate, poly(P-Dioxanone), and copolymers thereof); and thiols may be provided on some proteins. Alternatively, the surgical tape may be functionalized with tissue or substrate binding reactive groups, such as poly (lactic acid) and/or poly(glycolic acid), which include terminal carboxyl or hydroxyl groups.

The tissue reactive and/or self-reactive functional groups may be positioned on or near the first and second surfaces 62, 64 of surgical tape 60 using any suitable manner. For example, the surgical tape 60 may be formed from materials which naturally position reactive groups toward the outer surface of the surgical tape 60. In other examples, the surgical tape 60 may be surface-modified to covalently attach the reactive groups. In still other examples, the surgical tape 60 may be coated with an additional layer of material which includes the pendant reactive groups necessary to interact with the tissue and/or the surfaces of the surgical tape itself as described herein.

Methods for coating the surgical tape 60 are within the purview of those skilled in the art, and include but are not limited to spraying, dipping, brushing, vapor deposition, co-extrusion, capillary wicking, film casting, molding, and the like. The reactive groups may be combined with the surgical tape 60 in the form of a coating, film, foam, or powder on at least a portion of the first and second surfaces 62, 64, in embodiments on the entirety of the first and second surfaces 62, 64 of the surgical tape 60.

In embodiments utilizing a coating, the coating process may include surface treatment of the surgical tape 60 in order to promote adhesion of the coating to the first and second surfaces 62, 64 of the surgical tape 60. The first and second surfaces 62, 64 of the surgical tape 60 can be treated using plasma, physical or chemical vapor deposition, pulsed laser ablation deposition, surface modification, or any other means within the purview of those skilled in the art to activate the first and second surfaces 62, 64. In other embodiments, treatment may include the use of a primer such as a cross-linkable compound. In yet other embodiments, one or more deposition treatments could be used alone or in conjunction with the primer to achieve the desired association of coating with the first and/or second surfaces 62, 64 of the surgical tape 60.

In embodiments, the first and/or second surfaces 62, 64 may be functionalized by attaching a reactive component thereto. Suitable reactive components may include cross-linkers, adhesives, sealants, couplers, and the like that are functionalized with at least one reactive group capable of bonding the first and second surfaces 62, 64 to tissue "T" or with itself as described above.

Examples of adhesive that may be utilized on the first and/or second surfaces 62, 64, of the surgical tape 60 include, for example, adhesives which cure upon tissue contact, which cure upon exposure to ultraviolet (UV) light, which are two-part systems which are kept isolated from one another and cure upon coming into contact with one another, or any other known suitable adhesive. Other examples of adhesives include silicones, acrylics, polyurethanes, polyesters, polyamides, and rubber-based adhesives. Yet other examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively.

Leading tab 66 of surgical tape 60 may include a tissue reactive component 76 to adhere the tab 66 of the surgical tape 60 to tissue. The tissue reactive component 76 is applied to at least the surface of the leading tab 66 of the surgical tape 60 which is exposed to tissue during insertion of the surgical portal apparatus 10 into a wound. As illustrated, the tissue reactive component 76 is adhered to the first surface 62 of the surgical tape 60. The amount of time for the tissue reactive component 76 to bind to tissue may vary from about 30 seconds to about 20 minutes to allow time to insert, adjust, and properly position the sleeve 30 of the surgical portal apparatus 10 within tissue. In embodiments, the amount of time required to bind the tissue reactive component 76 to tissue is about 60 seconds to about 10 minutes, in some embodiments, about 3 minutes to about 7 minutes, and in yet other embodiments, about 5 minutes. Attachment of the tab 66 to surrounding tissue allows the body portion 65 of the surgical tape 60 to be unwound and released from the annular space 54 of the sleeve 30 upon rotation of the sleeve 30.

In embodiments, a hydrogel is utilized as the tissue reactive component 76 on the tab 66. Hydrogels include, for example, those using synthetic precursors within the purview of those skilled in the art, such as those used in commercially available products such as FocalSeal® from Genzyme, Inc., Coseal® from Angiotech Pharmaceuticals, and DuraSeal® from Confluent Surgical, Inc.

To use the surgical portal apparatus 10 of the present disclosure in connection with the performance of a surgical task during a surgical procedure, the seal housing 20 is mounted to the sleeve 30 as discussed above. The surgical portal apparatus 10 is introduced into a body cavity typically utilizing a sharp or non-blade trocar obturator to access the cavity and the obturator is removed. As illustrated in FIG. 4A, during placement of the sleeve 30 into a wound "W", the tissue reactive component 76 of the tab 66 is positioned against tissue "T" as the surgical portal apparatus 10 is being manipulated by a clinician into wound "W" so that the tissue reactive component 76 of the tab 66 forms a substantial bond with tissue "T" within a useful time range. A surgical instrument 12 (FIG. 1) may then be advanced through the surgical portal apparatus 10 and into the body cavity "C". The desired surgical task is performed with the surgical instrument 12 (FIG. 1). Upon completion of use, but prior to withdrawal of the surgical portal apparatus 10 from wound "W", the tab 66 should be sufficiently fixed to tissue "T" so that the clinician may rotate the sleeve 30 about longitudinal axis "b" (FIG. 1) to peel the body portion 65 of the surgical tape 60 off of the inner wall 50 (FIG. 2) of the sleeve 30 and onto the tissue "T". Thereafter, as shown in FIG. 4B, the surgical portal apparatus 10 is removed and the wound "W" is closed by the tissue reactive and/or self-reactive functional groups of the first and second surfaces 62, 64 of the surgical tape 60.

With reference now to FIGS. 5A and 5B, the leading tab 66 may be rotated out of the sleeve 30 at any time after placement of the surgical portal apparatus 10 within tissue by holding the outer wall 52 while rotating knob 21. Rotation of the knob 21 rotates the inner wall 50 of the sleeve 30 and thus the surgical tape 60, thereby moving the leading tab 66 out of the opening 56 in the outer wall 52. Alternatively, the knob 21 may be held still and the outer wall 52 rotated. Thereafter, upon fixation of the leading tab 66 to the tissue of the wound, the sleeve 30 may be rotated about the longitudinal axis "b" (FIG. 1), as described above, to unwind and release the body portion 65 of the surgical tape 60 from the annular space 54 of the sleeve 30. The surgical portal apparatus 10 may then be removed and the tissue closed.

Figure 6:
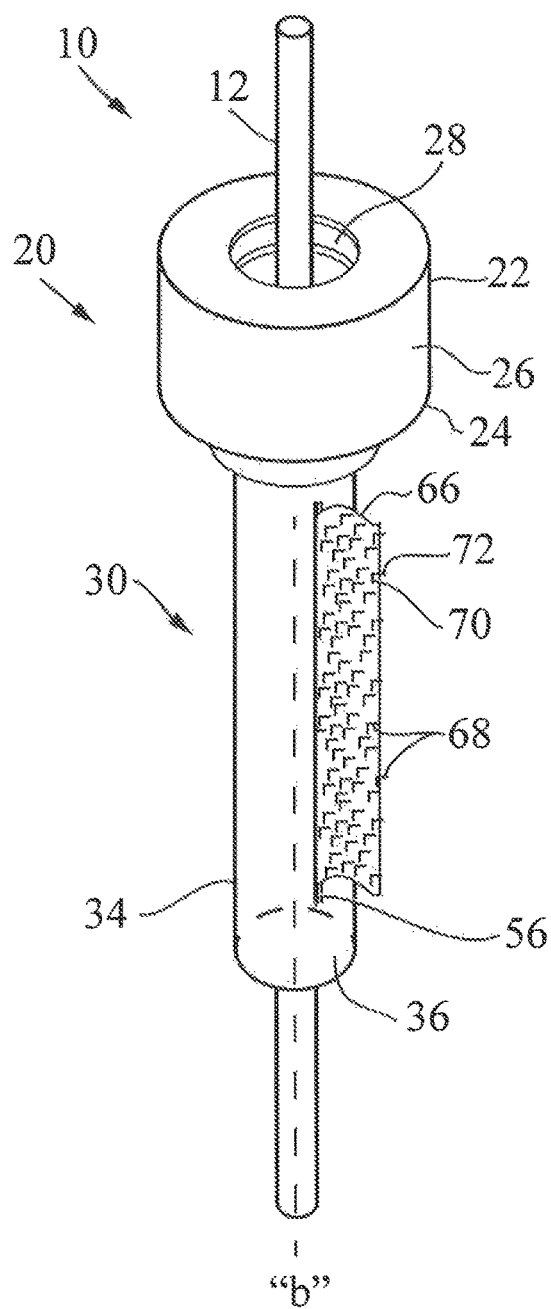
FIG. 6 is a perspective view of the surgical portal apparatus of FIG. 1 including a surgical tape in accordance with another embodiment of the present disclosure.

Additionally, or alternatively, as illustrated in FIG. 6, the tab 66 may include mechanical means for binding to tissue. In embodiments, the tab 66 may include mechanical grips or hooks 68 to achieve, or enhance, adhesivity to tissue. In embodiments, the mechanical grips 68 each include an arm 70 having a sharp or pointed distal end 72 extending in a direction transverse to the longitudinal axis "b" of the sleeve 30 to allow for longitudinal movement of the surgical portal apparatus 10 within tissue upon insertion and positioning of the sleeve 30 within the tissue, and piercing and gripping of the surgical tape 60 upon rotational movement of the surgical portal apparatus 10. Rotation of the surgical portal apparatus 10 fixes the tab 66 to tissue via the distal end 72 of the hooks 68 to effect release of the body portion 65 of the surgical tape 60 retained within the annular space 54 (FIG. 2) of the sleeve 30.

Figure 7:
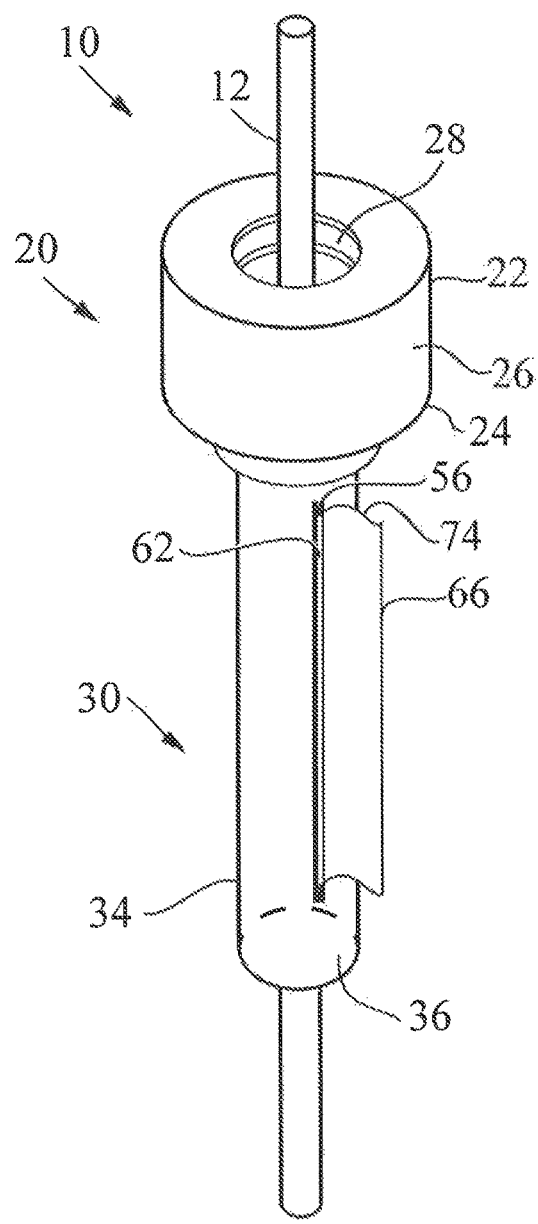
FIG. 7 is a perspective view of the surgical portal apparatus of FIG. 1 including a surgical tape in accordance with yet another embodiment of the present disclosure.

In yet other embodiments, as shown in FIG. 7, tab 66 may be covered by a release liner 74 formed from a quick dissolving or rapidly bioerodible polymeric material. Examples of quick dissolving or rapidly bioerodible polymer materials include water soluble polymers such as poly (lactide-co-glycolide)s, polyanhydrides, polyorthoesters, polyvinyl alcohol, and hydroxylpropyl methylcellulose; biopolymers such as sugars, starches, salts, and gelatin; and derivatives and combinations thereof. Release liner 74 may be applied to tab 66 by pressing, snap fitting, dipping, spraying, molding, or other forming processes within the purview of those skilled in the art. The release liner 74 may dissolve in a sufficient amount of time to allow for placement of the sleeve 30 of the surgical portal apparatus 10 within tissue. The release liner 74 may dissolve, deform, or drop off of the tab 66 exposing the reactive groups on the first surface 62 of the surgical tape 60.

Figure 8A:
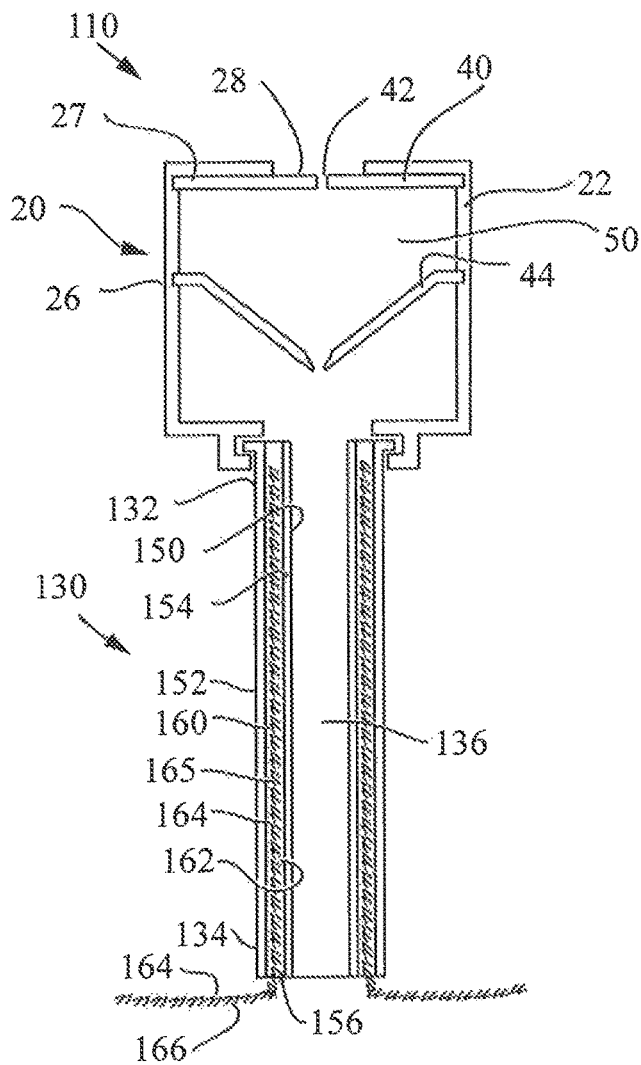
FIGS. 8A and 8B are cross-sectional and end views, respectively, of another embodiment of a surgical portal apparatus including a surgical tape in accordance with the principles of the present disclosure.

FIG. 8A illustrates another embodiment of the presently described surgical portal apparatus shown generally as 110. Surgical portal apparatus 110 includes a seal housing 20 mounted to sleeve 130. Sleeve 130 includes a proximal end portion 132 and a distal end portion 134 and defines an internal longitudinal passageway 136 dimensioned to permit introduction and passage of surgical instruments 12 (FIG. 1) therethrough. Sleeve 130 includes an inner wall 150 and an outer wall 152 defining a substantially cylindrical, annular space 154 therebetween similar to the embodiments of FIGS. 1-3. It should be understood that the surgical portal apparatus of FIG. 8A is similar to the surgical portal apparatus of FIGS. 1-3 and therefore will only be described with respect to the differences therebetween.

Figure 8B:
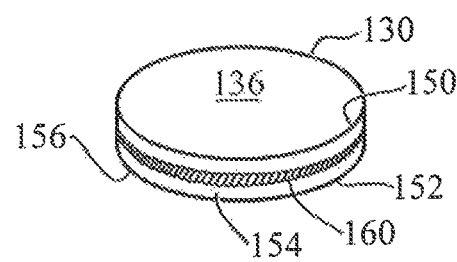

The annular space 154 defined between the inner wall 150 and the outer wall 152 may extend through the entire length of the circumference of the sleeve 130, or only through a portion or arc of the circumference of the sleeve 130 that is proportional to the size of the surgical tape 160, as shown in FIG. 8B. Sleeve 130 includes an opening 156 in the form of an annular slot, or annular sector thereof, in the distal end portion 134 of the sleeve 130. Surgical tape 160 is positioned within the annular space 154 of the sleeve 130 and includes a radially extending tab 166 in the form of a flange extending through the opening 156 formed in the distal end portion 134 of the sleeve 130. Tab 166 includes a tissue reactive component, mechanical grips, and/or a release liner positioned on the second surface 164 of the surgical tape 160 to adhere the tab 166 of the surgical tape 60 to tissue.

Figure 9A:
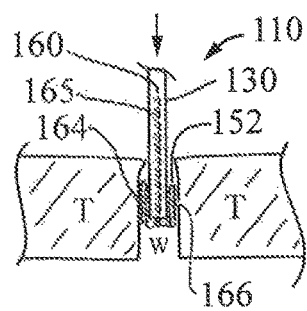
FIGS. 9A and 9B are cross-sectional schematic illustrations of the surgical portal apparatus of FIGS. 8A and 8B being positioned within tissue and removed from tissue, respectively, in accordance with an embodiment of the present disclosure.
Figure 9B:
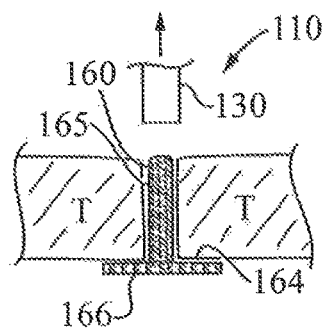
Figure 9C:
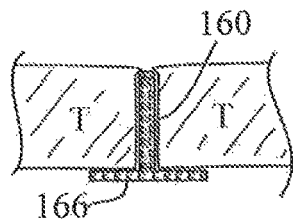
FIG. 9C is a cross-sectional schematic illustration of the surgical tape of FIGS. 9A and 9B positioned within tissue in accordance with an embodiment of the present disclosure.
Figure 10:
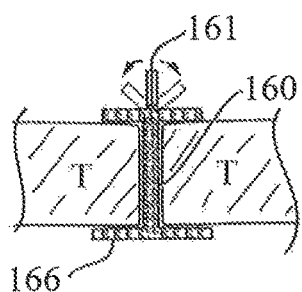
FIG. 10 is a cross-sectional schematic illustration of a surgical tape positioned within tissue in accordance with another embodiment of the present disclosure.

As illustrated in FIG. 9A, the second surface 164 of the surgical tape 160 is pressed against the outer wall 152 of the sleeve 130 and thus shielded from tissue "T" during insertion of the surgical portal apparatus 110 within wound "W". Once fully inserted within wound "W", as illustrated in FIG. 9B, the second surface 164 of the tab 166 is exposed to tissue "T" and fixes the surgical tape 160 against tissue "T" within a useful time range, as described above. Upon removal of the surgical portal apparatus 110 from the wound "W", the body portion 165 of the surgical tape 160 is released from the sleeve 130 via opening 156 and retained within wound "W". The first and second surfaces 162, 164 include reactive groups that are reactive with tissue "T" and/or that are self-reactive to aid in closing the wound "W", as illustrated in FIG. 9C. In some embodiments, such as that shown in FIG. 10, surgical tape 160 may include perforations 161 so that the surgical tape 160 may be bifurcated (shown in phantom). As illustrated, the surgical tape 160 extends from the wound "W" through the tissue surface "S" such that surgical tape 160 may be split and spread apart along perforations 161, in the direction of the arrows, to form its own bandage for closing tissue "T".

In some embodiments, at least one bioactive agent may be combined with the surgical tape of the present disclosure. The term "bioactive agent", as used herein, is used in its broadest sense and includes any substance or mixture of substances that have clinical use. A bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the substrate in any suitable form of matter, e.g., films, powders, liquids, gels, combinations thereof, and the like.

The bioactive agent may be included on any portion of the surgical tape. The bioactive agents may be incorporated into the surgical tape during formation of the surgical tape, such as by free suspension, liposomal delivery, microspheres, microparticles etc., or by coating a surface of the surgical tape, or portion thereof, such as by polymer coating, dry coating, and freeze drying. In embodiments in which the surgical tape is porous, bioactive agents may be incorporated within the pores thereof.

Examples of classes of bioactive agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used with the substrates of the present disclosure.

Other bioactive agents which may be included as a bioactive agent in the surgical tape of the present disclosure include: local anesthetics; non-steroidal antifertility agents;

parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-viral s; anticoagulants; anticonvulsants; antidepressants; antihistamines; and immunological agents.

Additional examples of suitable bioactive agents include viruses and cells; peptides; polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons ($\beta$-IFN, $\alpha$-IFN and $\gamma$-IFN); erythropoietin; nucleases; tumor necrosis factor; colony stimulating factors (e.g., GCSF, GM-CSF, MCSF); insulin; anti-tumor agents and tumor suppressors; blood proteins; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); protein inhibitors; protein antagonists and protein agonists; nucleic acids such as antisense molecules, DNA, and RNA; oligonucleotides; and ribozymes.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. A surgical portal apparatus comprising:
    a seal housing having proximal and distal portions and including a valve configured for maintaining a seal in the absence of a surgical object received through the seal housing; and
    a sleeve disposed on the distal portion of the seal housing and including proximal and distal ends defining a longitudinal axis, the sleeve including an inner wall extending from the proximal end of the sleeve to the distal end of the sleeve and defining an internal longitudinal passageway configured to permit passage of the surgical object through the passageway and out the distal end of the sleeve, and an outer wall extending from the proximal end of the sleeve to the distal end of the sleeve and configured to be positioned against tissue, the inner and outer walls defining at least a partial annular space therebetween, the annular space being in fluid communication with an opening in the outer wall, wherein the opening is defined by an unbroken circumference.

2. The surgical portal apparatus of claim 1, further including a surgical tape having a body portion retained within the annular space of the sleeve, and a leading tab extendable through the opening in the outer wall of the sleeve.

3. The surgical portal apparatus of claim 2, wherein the surgical tape includes a first surface and a second surface, at least one of the first and second surfaces having at least one of tissue reactive functional groups and self-reactive functional groups.

4. The surgical portal apparatus of claim 2, wherein the body portion of the surgical tape extends at least partially around the inner wall of the sleeve.

5. The surgical portal apparatus of claim 4, wherein the surgical tape is wrapped around the inner wall of the sleeve.

6. The surgical portal apparatus of claim 2, wherein the leading tab includes a tissue reactive component configured to attach the leading tab to tissue within about 30 seconds to about 20 minutes of tissue exposure.

7. The surgical portal apparatus of claim 2, wherein the leading tab includes mechanical hooks, and each hook includes an arm having a pointed distal end extending in a direction transverse to the longitudinal axis of the sleeve.

8. The surgical portal apparatus of claim 2, wherein the leading tab includes a release liner fabricated from a quick dissolving or rapidly bioerodible polymeric material positioned over at least one of first and second surfaces of the surgical tape.

9. The surgical portal apparatus of claim 2, wherein the surgical tape is selected from the group consisting of films, foams, meshes, fibrous sheets, patches, and composites thereof.

10. The surgical portal apparatus of claim 2, wherein the surgical tape is porous, non-porous, or combinations thereof.

11. The surgical portal apparatus of claim 2, wherein the opening in the outer wall of the sleeve is an annular slot formed in the distal end of the sleeve.

12. The surgical portal apparatus of claim 11, wherein the leading tab is an annular flange, the annular flange dimensioned and adapted to extend from the annular slot.

13. The surgical portal apparatus of claim 2, wherein the surgical tape includes perforations.

14. The surgical portal apparatus of claim 1, wherein the opening in the outer wall of the sleeve is a longitudinal slot.

15. The surgical portal apparatus of claim 14, wherein the longitudinal slot extends along substantially the entire length of the sleeve.

16. The surgical portal apparatus of claim 1, further comprising a rotatable knob attached to the inner wall.

17. The surgical portal apparatus of claim 1, wherein the surgical object is a surgical instrument.

18. The surgical portal apparatus of claim 1, wherein the inner wall is longitudinally fixed relative to the outer wall.

19. The surgical portal apparatus of claim 1, wherein the seal housing further includes a seal configured for receiving the surgical object in a sealing manner when the surgical object is received through the seal housing.

20. A surgical portal apparatus comprising:
a seal housing having proximal and distal portions and including a valve configured for maintaining a seal in the absence of a surgical object received through the seal housing; and
a sleeve disposed on the distal portion of the seal housing and including proximal and distal ends defining a longitudinal axis, the sleeve including an inner wall defining an internal longitudinal passageway configured to permit passage of a surgical instrument through the passageway and out the distal end of the sleeve, and an outer wall configured to be positioned against tissue, the inner and outer walls defining at least a partial annular space therebetween, the annular space being in fluid communication with an opening in the outer wall, wherein the opening is longitudinally spaced from the distal end of the sleeve.

21. A surgical portal apparatus comprising:
a seal housing having proximal and distal portions and including a valve configured for maintaining a seal in the absence of a surgical object received through the seal housing; and
a sleeve disposed on the distal portion of the seal housing and including proximal and distal ends defining a longitudinal axis, the sleeve including an inner wall defining an internal longitudinal passageway configured to permit passage of a surgical instrument through the passageway and out the distal end of the sleeve, and an outer wall configured to be positioned against tissue, the inner and outer walls defining at least a partial annular space therebetween, the annular space being in fluid communication with an opening in, and entirely bounded by, the outer wall.

* * * * *